US009066887B2

(12) United States Patent
Horstmann et al.

(10) Patent No.: US 9,066,887 B2
(45) Date of Patent: Jun. 30, 2015

(54) TRANSDERMAL THERAPEUTIC SYSTEM HAVING UREA COMPONENTS

(75) Inventors: Michael Horstmann, Neuwied (DE); Gerd Hoffmann, Neuwied (DE); Sandra Wiedersberg, Albersroda (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 527 days.

(21) Appl. No.: 12/865,465

(22) PCT Filed: Dec. 9, 2008

(86) PCT No.: PCT/EP2008/010426
§ 371 (c)(1),
(2), (4) Date: Jul. 30, 2010

(87) PCT Pub. No.: WO2009/095057
PCT Pub. Date: Aug. 6, 2009

(65) Prior Publication Data
US 2010/0310634 A1    Dec. 9, 2010

(30) Foreign Application Priority Data
Jan. 30, 2008  (DE) .......................... 10 2008 006 791

(51) Int. Cl.
*A61K 9/70* (2006.01)
*A61P 21/02* (2006.01)
*A61P 9/12* (2006.01)
*A61P 25/26* (2006.01)
*A61P 1/08* (2006.01)

(52) U.S. Cl.
CPC .................................... *A61K 9/7061* (2013.01)

(58) Field of Classification Search
None
See application file for complete search history.

(56) References Cited

U.S. PATENT DOCUMENTS

| | | | | |
|---|---|---|---|---|
| 3,981,996 | A | * | 9/1976 | Leigh .............................. 514/169 |
| 4,021,382 | A | * | 5/1977 | Stoy et al. ......................... 521/61 |
| 4,291,062 | A | * | 9/1981 | Leigh et al. .................... 514/588 |
| 4,687,481 | A | * | 8/1987 | Nuwayser ...................... 424/449 |
| 4,699,777 | A | * | 10/1987 | Zupon et al. ................... 514/588 |
| 5,230,896 | A | * | 7/1993 | Yeh et al. ........................ 424/443 |
| 5,730,999 | A | | 3/1998 | Lehmann et al. |
| 6,238,284 | B1 | | 5/2001 | Dittgen et al. |
| 6,280,765 | B1 | | 8/2001 | Gueret |
| 2004/0018241 | A1 | * | 1/2004 | Houze et al. ................... 424/486 |
| 2004/0033254 | A1 | * | 2/2004 | Song et al. ..................... 424/449 |
| 2007/0104772 | A1 | * | 5/2007 | Zanutto et al. ................. 424/449 |
| 2008/0279915 | A1 | | 11/2008 | Wilhelm |

FOREIGN PATENT DOCUMENTS

| | | |
|---|---|---|
| CA | 2114537 | 2/1993 |
| DE | 4210165 | 2/1993 |
| DE | 4210165 A1 | 2/1993 |
| DE | 19701949 | 7/1998 |
| DE | 19701949 A1 | 7/1998 |
| DE | 102004028284 | 1/2006 |
| DE | 102004028284 A1 | 1/2006 |
| EP | 0617972 | 3/1994 |
| EP | 0617972 A2 | 10/1994 |
| EP | 0870498 | 10/1998 |
| EP | 0870498 A1 | 10/1998 |
| FR | 2867978 | 9/2005 |
| FR | 2867978 A1 | 9/2005 |
| JP | 10-287559 | 5/1998 |
| WO | WO 93/02669 | 2/1993 |
| WO | WO-9302669 A1 | 2/1993 |
| WO | WO 97/39740 | 10/1997 |
| WO | WO 2004/047816 | 6/2004 |
| WO | WO-2004047816 A1 | 6/2004 |

OTHER PUBLICATIONS

Kim et al., "Effect of fatty acids and urea on the penetration of ketoprofen through rat skin", 1993; International J. of Pharmaceutics, 99:109-118.
Bentley et al., "The influence of lecithin and urea on the in vitro permeation of hydrocortisone acetate through skin from hairless mouse", 1997; International J. of Pharmaceutics, 146:255-262.
Wohlrab, "The Influence of Urea on the Penetration Kinetics of Topically Applied Corticosteroids", 1984; Acta Derm Venereol, 64:233-238.
Clarys et al., "A Qualitative Estimate of the Influence of Halcinonide Concentration and Urea on the Reservoir Formation in the Stratum Corneum", Skin Pharmacol Appl Skin Physiol, 1999; 12:85-89.
Valenta et al., "Effect of Urea and Pantothenol on the Permeation of Progesterone Through Excised Rat Skin from Polymer Matrix Systems", Drug Development and Industrial Pharmacy, 2001; 27(1), 57-62.
Valenta et al., "In Vitro Release Study of Transdermal Delivery Systems of Progesterone", Drug Development and Industrial Pharmacy, 1998; 24(2), 187-191.
Yamakawa T, et al.; Patech containing 1,2-ethanediol derivatives or salts thereof; (1997) pp. 1-2 XP002561598.
Valenta C and Dabic T; Effect of Urea and Pantothenenol on the Permeation of Progesterone Through Excised Rat Skin from Polymer Matrix Systems, Drug Development and Industrial Pharmacy (2001) vol. 27(1), pp. 57-62.
Valenta C and Biebel R; *In Vitro Release Study of Transdermal Delivery Systems of Progesterone*, Drug Development and Industrial Pharmacy (1998) vol. 24(2) pp. 187-191.
Trottier R and Wood S; *Particle Size Measurement*; Kirk-Othmer Encyclopedia of Chemical Technology (2005) http://www.mrw.interscience.wiley.com/kirk/articles/sizetrot.a01/sect1.html Article Online Posting Date: Oct. 14, 2005.
Schmid, H, *There's more than one way to measure powder particle size!*, Metal Powder Report, vol. 58, iss.11, p. 26-31 (Nov. 2003).

* cited by examiner

*Primary Examiner* — Susan Tran
*Assistant Examiner* — William Craigo
(74) *Attorney, Agent, or Firm* — Frommer Lawrence & Haug LLP

(57) ABSTRACT

The invention relates to a transdermal therapeutic system (TTS) for administering pharmaceutical agents through the skin, comprising a back layer (R) impermeable to the agent and at least one layer (S) comprising the agent, wherein the layer (H) facing the skin comprises urea in solid form, allowing continuous administration of large quantities of agent over a long period of time.

15 Claims, 4 Drawing Sheets

TRANSDERMAL THERAPEUTIC SYSTEM HAVING UREA COMPONENTS

Transdermal therapeutic systems (TTS) are pharmaceutical administration forms which are applied to the skin of a mammalian organism and are designed to make a drug available systemically following transdermal absorption. TTS are able to increase the therapeutic value of drug administration by ensuring constant delivery of the active ingredient into the blood compartment over a prolonged time period. The advantages of this continuous delivery of active ingredient are, primarily, the extended intervals of application, leading to improved patient compliance, and the pharmacokinetically optimized plasma concentration/time profile, which ensures a longer duration of action with fewer side effects. Further advantages occasioned by the transdermal application route by means of a TTS are reduced dosage, improved gastrointestinal compatibility, and improved bioavailability as a result of avoidance of the first-pass effect.

On the basis of these advantages, TTS have for some years enjoyed a growing popularity for the therapy of a variety of illnesses. Systems of this kind have been introduced into therapy for—for example—the active ingredients estradiol, nicotine, norethisterone acetate, fentanyl, tulobuterol, ethinylestradiol, buprenorphine, and nitroglycerine. A TTS construction is generally thin and layered, and thus produces, with the aid of the layer (H) directly facing the skin, an at least temporarily adhesive bond to the skin, via which the active ingredient is delivered. TTS are typically composed of a drug-impermeable backing layer (R); an active-ingredient-containing layer (S), a reservoir layer or matrix layer, for example, and an adhesive layer (K) for attachment to the skin, this layer possibly being identical with the drug-containing or ingredient-containing layer (e.g., reservoir layer or matrix layer), and a drug-impermeable protective layer (A), referred to as the release liner, which is intended for removal prior to application.

In order to improve the permeation of the particular active ingredient through the skin, use is made, in addition to various solid polymers (e.g., polyacrylates, silicones, polyisobutylenes), resins, and other pharmaceutical auxiliaries, of various system components which are liquid at room temperature and which in part allow adjustment of the bond strength and serve to enhance diffusion within the transdermal therapeutic system or else to enhance permeation of the active ingredient through the skin.

Many of the known active ingredients are suitable for administration via the skin—for example, because their low molecular weight and/or their high lipophilicity allow them to pass through the human skin even without further, auxiliary measures. Examples of such active ingredients are the ingredients nicotine, nitroglycerine, steroid hormones, and clonidines. For many active pharmaceutical ingredients, however, administration via the transdermal route has been closed off to date, because their daily dose is too high to be administered via a reasonable area of skin.

Numerous technical solutions have already been proposed, such as the addition of permeation promoters, the application of electrical voltage (iontophoresis) or ultrasound, and use of skin microlesions, and at least to some extent have also been successfully tested experimentally. There are a number of possibilities for increasing active ingredient flux through the skin. In general, however, these measures are accompanied by restricted compatibility with the skin, thus requiring the medic to make a risk assessment, which then usually comes down in favor of a conventional administration form.

It is an object of the present invention to provide a transdermal therapeutic system which significantly boosts the flux of active ingredient through the skin and at the same time exhibits good (or at least acceptable) skin compatibility.

The object of the invention is achieved through the addition of the auxiliary urea, in solid form, which is already present in small amounts in any case in the skin of the mammalian organism (e.g., humans).

The use of urea in general form as a permeation promoter is not fundamentally unknown. A promotive effect of urea on skin permeation is described, for example, by W. Wohlrab (Acta Derm. Venerol 1984, 64, 233-238), where a formulation of hydrocortisone as an emulsion with urea is presented.

C. K. Kim (Intern. J. of Pharmaceutics 1993, 99, 109-118) describes the effect of urea solutions on the penetration of ketoprofen through the skin of mice.

The publication by V. L. B. Bentley (Intern. J. of Pharmaceutics 1997, 146, 255 to 262) discloses the increase in permeation achieved for hydrocortisone by means of urea-containing gels. The effect of urea on human skin is also described by P. Clarys (Skin Pharmacology and Applied Skin Physiology 1999, 12, 85-89).

To date, however, no standard commercial systems have been known which use a high proportion of solid urea in the form of coarse particles.

DETAILED DESCRIPTION OF EMBODIMENTS

Figure 1:
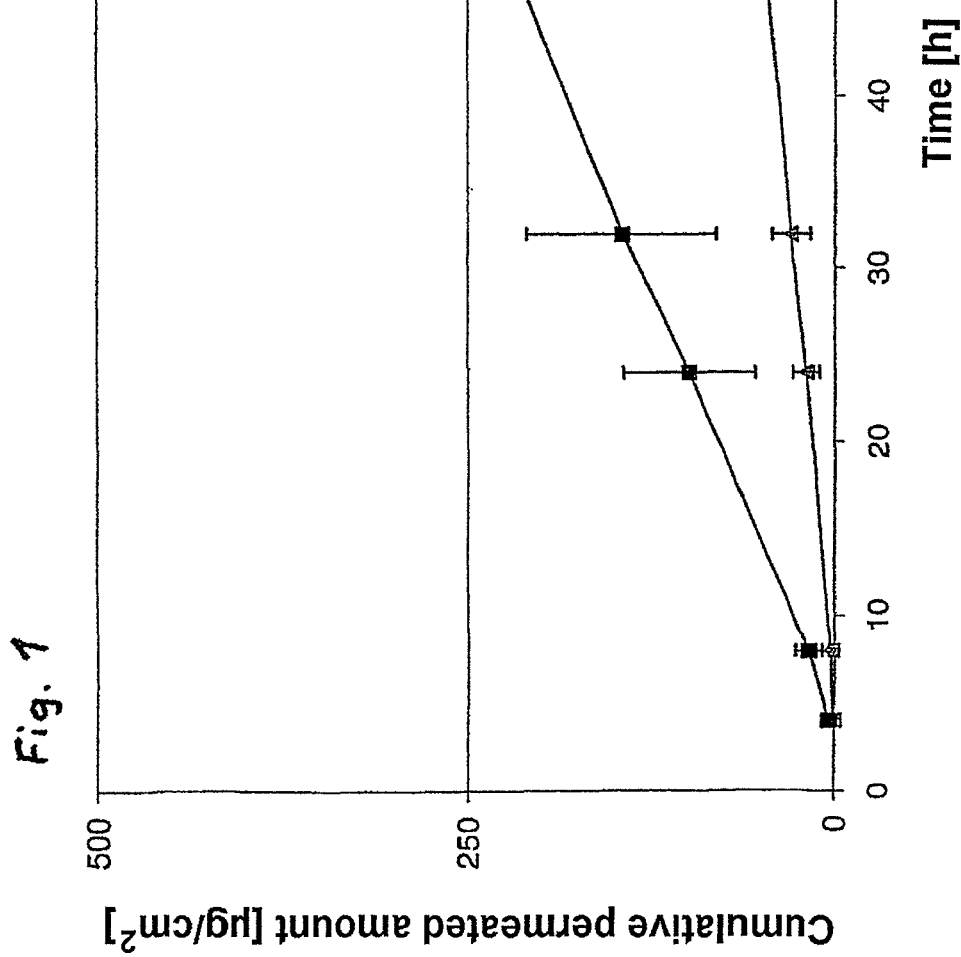
FIGS. 1-4 show the cumulative permeated amount of an active ingredient (in µg per cm2) as the ordinate, and the time (in hours) as the abscissa, for TTSs. The curves marked with small triangles in FIGS. 1, 2, and 4 show the results for TTS without addition of urea, while those marked with small squares show the results with a 20% addition of urea (the particle size being 90 to 125 µm).

The present invention provides a transdermal therapeutic system (TTS) for delivering active pharmaceutical ingredients through the skin, comprising an ingredient-impermeable backing layer (R) and at least one ingredient-containing layer (S), wherein the skin-facing layer (H) comprises solid urea.

In the TTS the weight fraction (more precisely water fraction) of the urea as a proportion of the base material of the skin-facing layer (H) of the TTS is preferably at least 20% (m/m).

The invention further provides a TTS wherein the urea present in layer (H) is present substantially in solid, coarsely crystalline form.

The invention also provides a TTS wherein the ingredient-containing layer (S) is also the skin-facing layer (H), and this layer, in addition to 1% to 20% (m/m), more particularly from 1% to 15% (m/m), of at least one active pharmaceutical ingredient, comprises 20% to 50% (m/m) of urea.

Also provided is a TTS wherein the urea present in layer (H) is present to an extent of at least 50% by weight in a particle size of more than 50 µm, preferably more than 70 g, and more particularly more than 100 µm. The particle size and particle size distribution can be measured, for example, using sieves.

The invention also provides a TTS wherein the urea present in layer (H) is present to an extent of at least 70% by weight in a particle size of more than 70 µm.

The invention also provides a TTS wherein the crystalline urea present in layer (H) is present to an extent of at least 70% by weight in a particle size of more than 100 µm.

The invention also relates to a TTS wherein the ingredient-containing layer (S) is a polymer matrix, more particularly a polyacrylate matrix, which, in addition to 2% to 18% (m/m) of at least one active pharmaceutical ingredient, comprises 20% to 40% (m/m) of urea.

The invention also provides a TTS where the ingredient-containing layer (S) is a polymer matrix based on a polyacrylate and/or a polymethacrylate which, in addition to 5% to 18% (m/m) of at least one active pharmaceutical ingredient, comprises 20% to 60% (m/m) of urea, which is present to an extent of at least 50% by weight in a particle size of more than 50 µm, preferably more than 70 g, and more particularly more than 100 µm.

The invention also provides a TTS wherein the ingredient-containing layer (S) is a polymer matrix based on a polyacrylate and/or a polymethacrylate, which, in addition to an active pharmaceutical ingredient from the group consisting of muscle relaxants, antihypertensives, psychostimulants, and antiemetics, comprises 20% to 40% (m/m) of crystalline urea which is present to an extent of at least 70% by weight in a particle size of more than 70 µm (and more particularly more than 100 µm).

The invention also provides methods of producing a transdermal therapeutic system as described above, wherein at least one ingredient-containing layer (S) and, if desired, further layers are applied to an ingredient-impermeable backing layer (R), the skin-facing layer (H) comprising urea in solid, preferably crystalline, form.

A further aspect is the use of an active-ingredient-containing polymer layer (S) further comprising solid urea for producing a pharmaceutical formulation for treating illnesses in humans and animals.

On the basis of the experimental results below, it proved surprising that, in contrast to dissolved or finely divided urea, the addition of solid urea, present in the form of coarse particles and in a proportion of at least 20%, produces a significant boost to permeation which is very relevant in its order of magnitude.

The permeation-enhancing effect of the solid urea in the form of coarse particles was demonstrated for different active-ingredient groups such as, for example, muscle relaxants (tizanidine), antihypertensives (moxonidine), psychostimulants (caffeine), and antiemetics (lerisetron).

The associated TTS construction is preferably multilayered and comprises at least one ingredient-containing layer(s) and an adhesive layer, where the ingredient-containing layer can also be the adhesive layer. Having proved particularly suitable is a TTS in which the adhesive layer of the system has a urea fraction of at least 20% (m/m).

The urea present is preferably present, to an extent of at least 80%, in solid form, as coarse particles. The coarse, solid particles again preferably have a particle size of at least 50 µm, more preferably more than 70 µm, and more particularly of more than 100 µm. The urea used may preferably be a crystalline urea.

Figure 2:
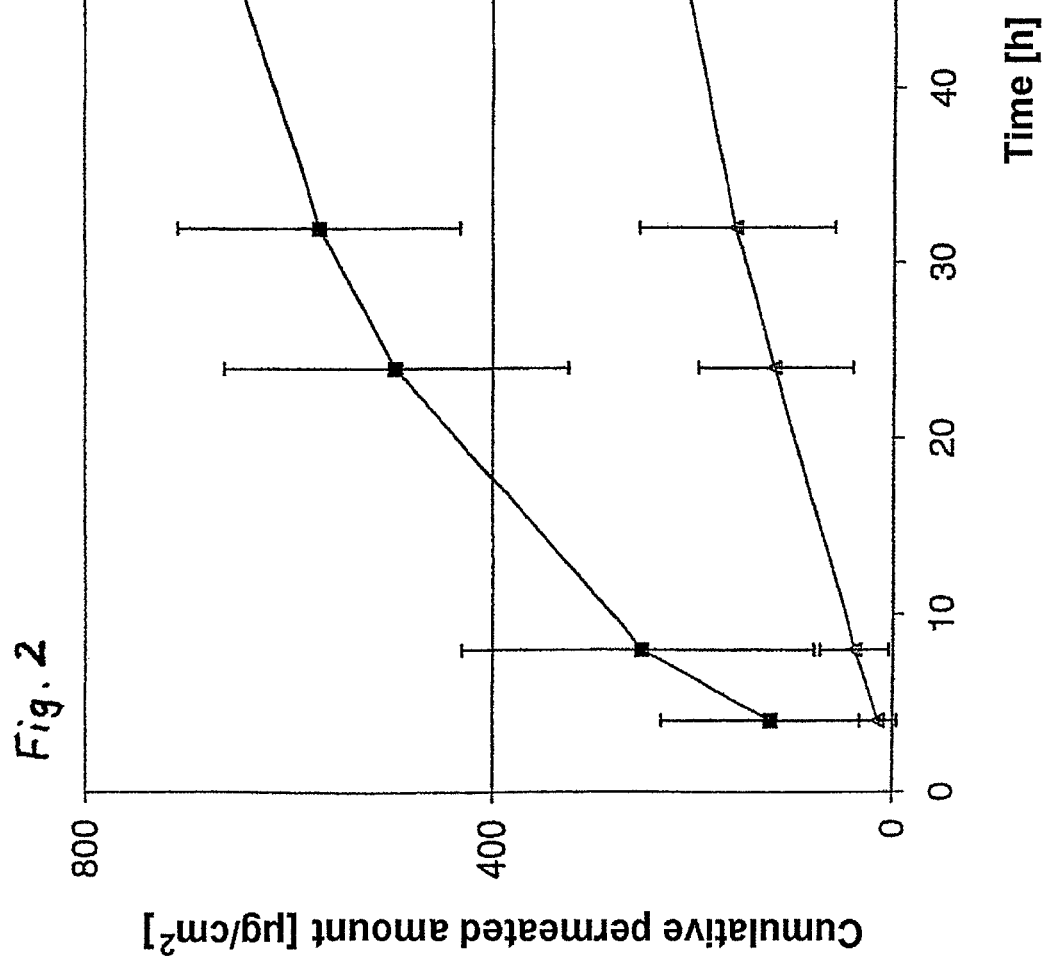

The invention is illustrated with the examples below. The drawings (FIGS. 1 to 4) show the cumulative permeated amount of the active ingredient (in µg per cm$^2$) as the ordinate, and the time (in hours) as the abscissa. The curves marked with small triangles in FIGS. 1, 2, and 4 show the results for TTS without addition of urea, while those marked with small squares show the results with a 20% addition of urea (the particle size being 90 to 125 µm). A significant increase in permeation can be seen, by a factor of 4 to 9, for different active ingredients, as a result of the addition of solid urea.

Figure 3:
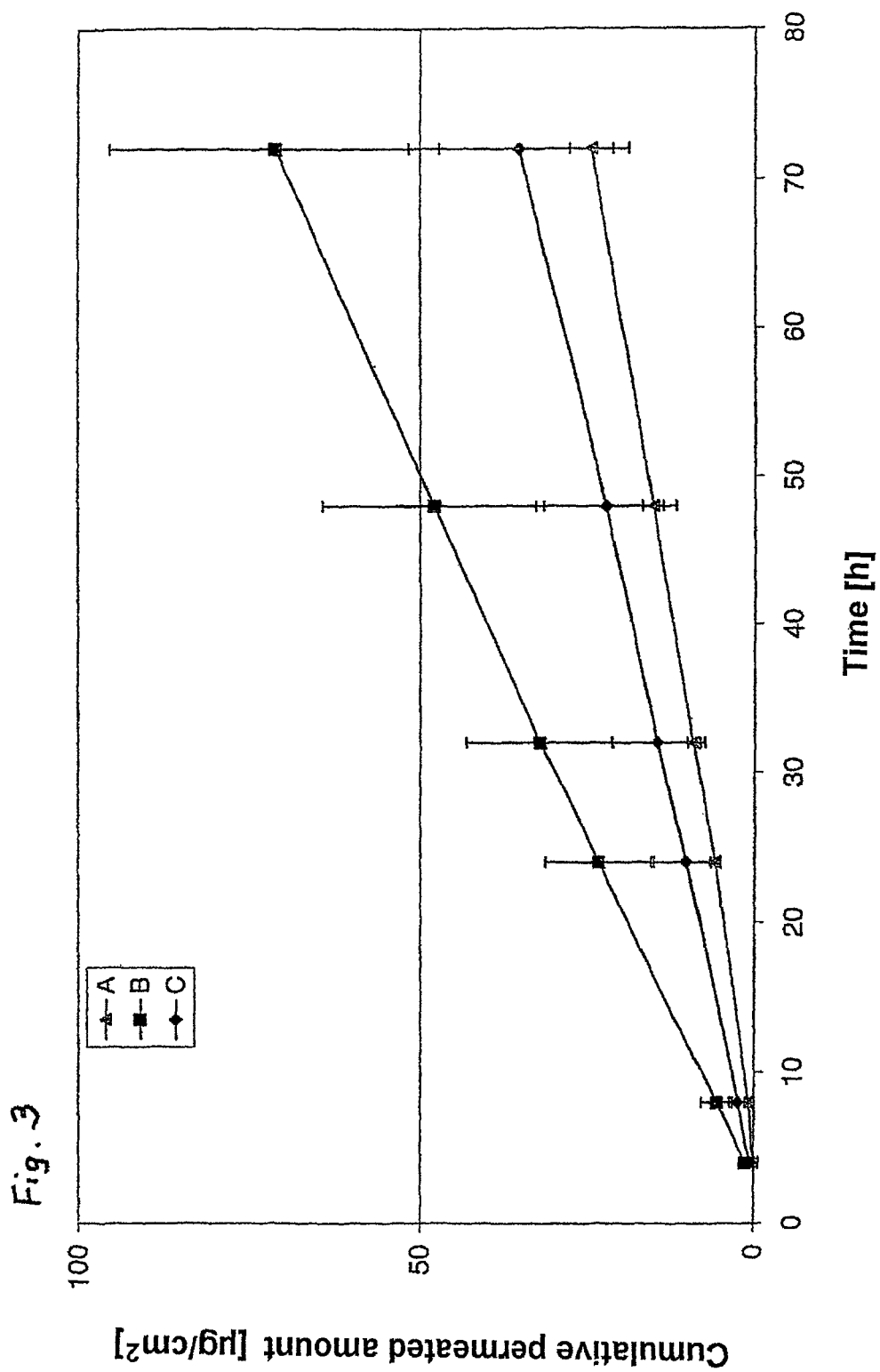
Figure 4:
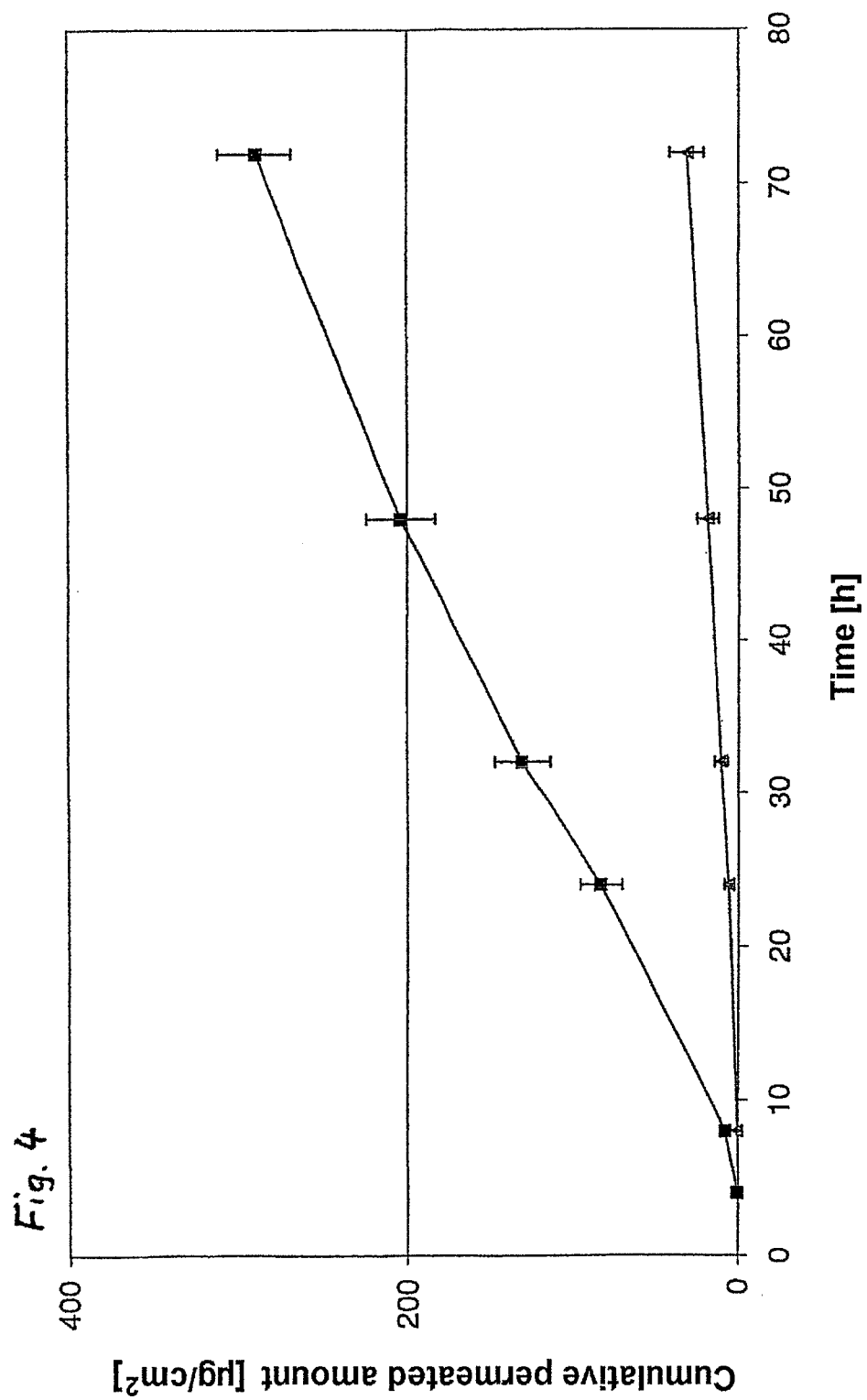

FIG. 3 shows an unexpectedly significant increase in the active ingredient permeation of the TTS with urea in a particle size>100 µm (curve B) relative to the comparative example of a TTS with urea having a particle size<50 µm (curve C). Curve A in FIG. 3, marked with small triangles, shows the results for TTS without addition of urea.

EXAMPLE 1

Construction of a Matrix System TTS

Peelable protective layer (silicone-coated PET film)
Adhesive layer: hydrophilic acrylate adhesive (for example, Durotak® 387-2287) with 10% (m/m) tizanidine and 20% (m/m) urea, the urea being present in solid form as coarse particles having a particle size>100 µm.
Occlusive film (PET film)

A commercial acrylate adhesive was dissolved in a solvent. The acrylate adhesive solution was admixed with the active ingredient tizanidine and with solid urea in the form of coarse particles, in the quantities identified above, with stirring. This acrylate adhesive composition was cast to form a reservoir layer 500 µm in thickness, and the solvent was evaporated, producing a matrix basis weight of 100 g/m$^2$. A number of experimental TTS were punched from this active ingredient laminate, and were then used for experiments in vitro.

The in vitro permeation experiments were carried out in a Franz diffusion cell, which is described in the prior art. The Franz diffusion cell is composed of a donor compartment and an acceptor compartment, separated by a membrane (cow udder). The donor compartment contains the TTS, while, for the acceptor compartment, a physiological buffer was used, conditioned to a temperature of 32° C. Samples were taken from the acceptor compartment over a period of 72 h, and were analyzed by HPLC for the permeated amount of active ingredient.

The test results are shown in FIG. 1 in the form of the permeation profile of the active ingredient through cow udder. The cumulative permeated amount of active ingredient (micrograms per square centimeter) from a TTS containing no urea (A) and from a TTS containing urea in a particle size>100 µm (B) was plotted against the time. The significant increase in tizanidine permeation through the skin, by a factor of 4, can be seen.

EXAMPLE 2

Construction of a Matrix System TTS

Peelable protective layer (silicone-coated PET film)
Adhesive layer: hydrophilic acrylate adhesive (for example, Durotak 387-2287) with 10% (m/m) caffeine and 20% (m/m) urea, the urea being present in crystalline form having a particle size>100 µm.
Active-ingredient-free layer (36 g/m$^2$): hydrophobic polymer blended with a resin (for example, Kraton®/Foral; ¼)
Occlusive film (PET film)

The TTS was produced and investigated as described in example 1. The cumulative permeated amount of active ingredient (micrograms per square centimeter) from a TTS containing no urea (A) and from a TTS containing urea in a particle size>100 µm (B) was plotted against the time (FIG.

2). The significant increase in caffeine permeation through the skin, by a factor of 8, can be seen.

EXAMPLE 3

Construction of a Matrix System TTS

Peelable protective layer (silicone-coated PET film)
Adhesive layer: hydrophilic acrylate adhesive (for example, Durotak® 387-2287) with 10% (m/m) moxonidine and 20% (m/m) urea; the urea being present in crystalline form having a particle size>100 µm.
Occlusive film (PET film)
The TTS was produced and investigated as described in example 1. The cumulative permeated amount of active ingredient (micrograms per square centimeter) from a TTS containing no urea (A), a TTS containing 10% urea with a particle size<50 µm (C), and from a TTS containing 20% urea in a particle size>100 µm (B) was plotted against the time (FIG. 3). The significant increase in the permeation of moxonidine as a result of the 20% urea fraction with a particle size>100 µm can be seen.

EXAMPLE 4

Construction of a Matrix System TTS

Peelable protective layer (silicone-coated PET film)
Adhesive layer: hydrophilic acrylate adhesive (for example, Durotak® 387-2287) with 10% (m/m) lerisetron and 20% (m/m) urea, the urea being present in crystalline form having a particle size>100 µm.
Occlusive film (PET film)
The TTS was produced and investigated as described in example 1.
The cumulative permeated amount of lerisetron was plotted against the time and is shown in FIG. 4. The cumulative permeated amount of active ingredient (micrograms per square centimeter) from a TTS containing no urea (A) and from a TTS containing urea in a particle size>100 µm (B) was plotted against the time (FIG. 4). The significant increase in the permeation of lerisetron through the skin, by a factor of 9, can be seen.

The invention claimed is:

1. A transdermal therapeutic system (ITS) for delivering active pharmaceutical ingredients through the skin, comprising:
an ingredient-impermeable backing layer (R);
at least one ingredient-containing layer (S) comprising at least one active pharmaceutical ingredient; and
a skin-facing layer (H) comprising solid urea in the form of coarse solid particles;
wherein the weight fraction of the solid urea, as a proportion of the base material of the skin-facing layer (H) of the TTS, is at least 20% (m/m);
wherein, among all the solid urea in the skin-facing layer (H), at least 50% by weight of the solid urea have a particle size of more than 50 µm; and
wherein the ingredient-containing layer (S) is the same or is different from the skin-facing layer (H).

2. The transdermal therapeutic system of claim 1;
wherein the solid urea present in the skin-facing layer (H) is present substantially in solid crystalline form.

3. The transdermal therapeutic system of claim 1;
wherein the ingredient-containing layer (S) is the same as the skin-facing layer (H);
wherein the at least one active pharmaceutical ingredient is present in the ingredient-containing layer (S) in an amount of 1% to 20% (m/m); and
wherein the solid urea is present in the ingredient-containing layer (S) in an amount of 20% to 50% (m/m).

4. The transdermal therapeutic system of claim 1;
wherein, among all the solid urea present in the skin-facing layer (H), at least 70% of the solid urea by weight have a particle size of more than 50 µm.

5. The transdermal therapeutic system of claim 1;
wherein, among all the solid urea present in the skin-facing layer (H), at least 50% of the solid urea by weight have a particle size of more than 70 µm.

6. The transdermal therapeutic system of claim 5;
wherein, among all the solid urea present in the skin-facing layer (H), at least 70% of the solid urea by weight have a particle size of more than 70 µm.

7. The transdermal therapeutic system of claim 1;
wherein, among all the solid urea present in the skin-facing layer (H), at least 50% of the solid urea by weight have a particle size of more than 100 µm.

8. The transdermal therapeutic system of claim 7;
wherein, among all the solid urea present in the skin-facing layer (H), at least 70% of the solid urea by weight have a particle size of more than 100 µm.

9. The transdermal therapeutic system of claim 1;
wherein the ingredient-containing layer (S) is the same as the skin-facing layer (H), and includes a polymer matrix;
wherein the at least one active pharmaceutical ingredient is present in the polymer matrix in an amount of 2% to 18% (m/m),
wherein the solid urea is present in the polymer matrix in an amount of 20% to 40% (m/m).

10. The transdermal therapeutic system of claim 1;
wherein the ingredient-containing layer (S) is the same as the skin-facing layer (H), and includes a polymer matrix based on a polyacrylate and/or a polymethacrylate;
wherein the at least one active pharmaceutical ingredient is present in the polymer matrix in an amount of 5% to 18% (m/m);
wherein the solid urea is present in the polymer matrix in an amount of 20% to 60% (m/m); and
wherein, among all the urea, at least 50% of the urea by weight have a particle size of more than 50 µm.

11. The transdermal therapeutic system of claim 1;
wherein the ingredient-containing layer (S) is the same as the skin-facing layer (H), and includes a polymer matrix based on a polyacrylate and/or a polymethacrylate;
wherein the active pharmaceutical ingredient is present in the polymer matrix, and comprises at least one ingredient selected from the group consisting of muscle relaxants, antihypertensives, psychostimulants, and antiemetics;
wherein the solid urea is crystalline urea, and is present in the polymer matrix in an amount of 20% to 40% (m/m); and
wherein, among all the crystalline urea, at least 70% of the crystalline urea by weight have a particle size of more than 70 µm.

12. The transdermal therapeutic system of claim 1;
wherein the solid urea present in layer (H) is present substantially in solid crystalline form;
wherein the ingredient-containing layer (S) is the same as the skin-facing layer (H), and includes a polymer matrix based on a polyacrylate and/or a polymethacrylate;

wherein the at least one active pharmaceutical ingredient is present in the polymer matrix in an amount of 5% to 18% (m/m);

wherein the solid urea is present in the polymer matrix in an amount of 20% to 60% (m/m); and wherein, among all the urea, at least 50% of the urea by weight have a particle size of more than 50 μm.

13. A method of producing a transdermal therapeutic system as claimed in claim 1, comprising:

applying the at least one ingredient-containing layer (S) and the skin-facing layer (H), and optionally further layers, to the ingredient-impermeable backing layer (R);

wherein the ingredient-containing layer (S) is the same or is different from the skin-facing layer (H).

14. A method of treating an illness, comprising:

administering the transdermal system of claim 1 to a patient.

15. The method of claim 14;

wherein the solid urea present in layer (H) is present substantially in solid crystalline form;

wherein the ingredient-containing layer (S) is the same as the skin-facing layer (H), and includes a polymer matrix based on a polyacrylate and/or a polymethacrylate;

wherein the at least one active pharmaceutical ingredient is present in the polymer matrix in an amount of 5% to 18% (m/m);

wherein the solid urea is urea is present in the polymer matrix in an amount of 20% to 60% (m/m).

\* \* \* \* \*